US007013599B2

(12) United States Patent
Smith et al.

(10) Patent No.: US 7,013,599 B2
(45) Date of Patent: Mar. 21, 2006

(54) METHODS AND MIXTURES FOR TREATING DISTRESSED TREES

(76) Inventors: Don Wiley Smith, 2107 Emerson La., Denton, TX (US) 76201; Peter Martin, 413 Meng Cir., Denton, TX (US) 76201

( * ) Notice: Subject to any disclaimer, the term of this patent is extended or adjusted under 35 U.S.C. 154(b) by 0 days.

(21) Appl. No.: 10/808,156

(22) Filed: Mar. 24, 2004

(65) Prior Publication Data

US 2004/0194372 A1    Oct. 7, 2004

Related U.S. Application Data

(63) Continuation of application No. 09/660,257, filed on Sep. 12, 2000, now abandoned.

(51) Int. Cl.
*A01G 7/06* (2006.01)
(52) U.S. Cl. .............................. 47/58.1 R; 47/58.1 SC
(58) Field of Classification Search ............. 47/58.1 R, 47/58.1 SC
See application file for complete search history.

(56) References Cited

U.S. PATENT DOCUMENTS 4,872,899 A * 10/1989 Miller ......................... 71/11

FOREIGN PATENT DOCUMENTS

| DE | 231 2051 | 12/1974 |
|----|----------|---------|
| DE | 360 0340 | 9/1987 |
| EP | 107 450 A | 2/1984 |
| GB | 2 152 492 A | 7/1985 |
| WO | WO 99 07654 | 2/1999 |

OTHER PUBLICATIONS

Dale, Fred. Apr. 5, 1987. April is transplant time, Special to the Star. p. C9.*
Anonymous. 1997. Green Light Rotone.*
Howard Garett. Nov. 26, 1999. The time os not ripe to start sweet potatoes. p. 4G.*
Anonymous. 1998. Merriam-Webster's Collegiate Dictinary, 10th ed., p. 1258.*
Tisdale and Nelson. 1975. Soil Fertility and Fertilizers, 3rd ed., Macmillan Publishing Co., p. 506.*
Journal of Horticultural Science and Biotechnology, May, 1998, vol. 73, No. 3, Pg. 353-359 article entitled "The Influence of Plant Growth Regulators on Root and Shoot Growth of Containerized Trees Following Root Removal" by Percival, G. and.

* cited by examiner

*Primary Examiner*—Jeffrey L. Gellner
(74) *Attorney, Agent, or Firm*—John E. Vandigriff

(57) ABSTRACT

A method of treating a distressed tree includes the steps of: creating a mixture comprising a fertilizer and a growth hormone and applying the mixture to a root area of the distressed tree.

7 Claims, 2 Drawing Sheets

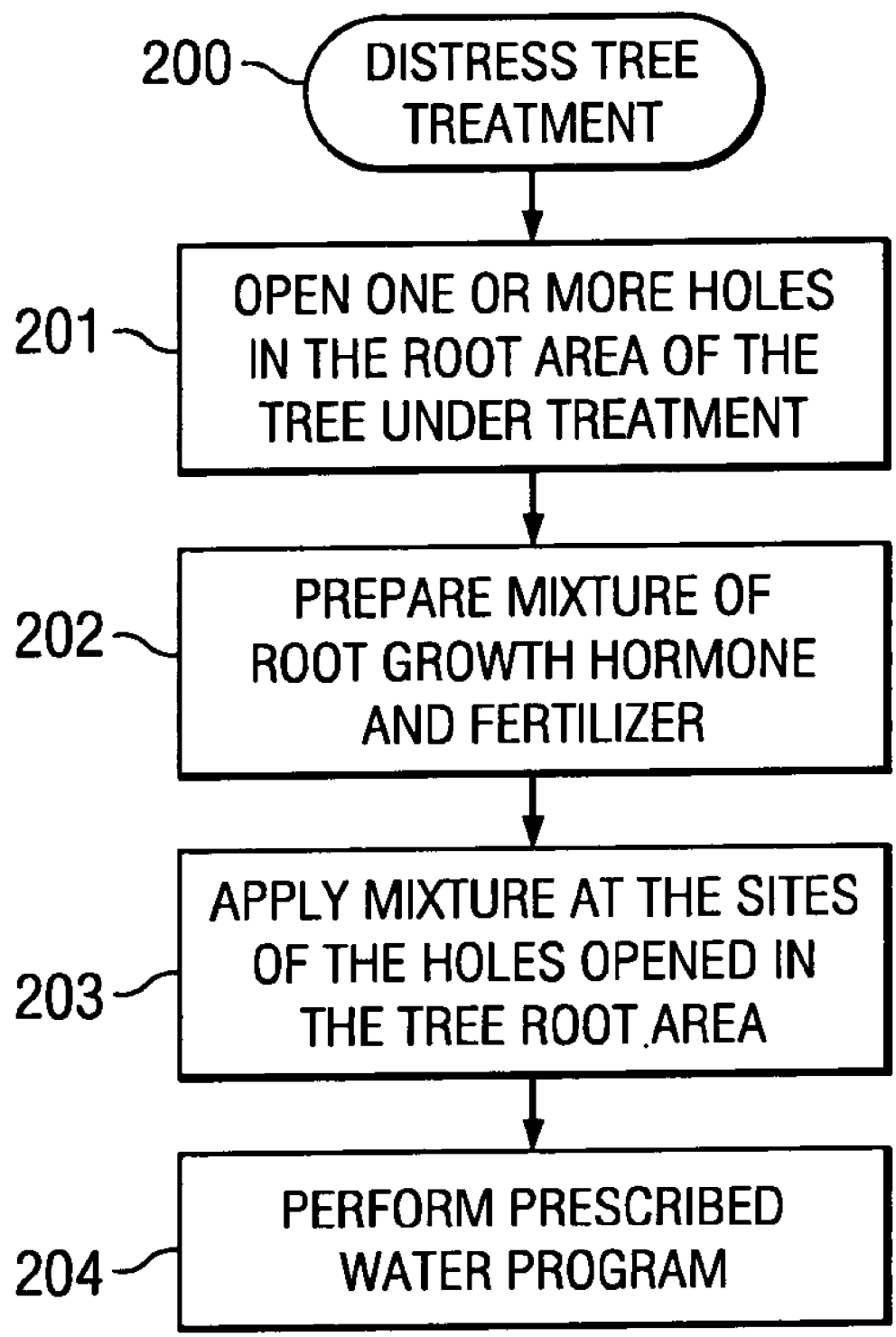

METHODS AND MIXTURES FOR TREATING DISTRESSED TREES

CROSS REFERENCE TO RELATED APPLICATIONS

This application is a continuation of U.S. Ser. No. 09/660,257, by Smith, et al. entitled "Methods And Mixtures For Treating Distressed Trees", filed Sep. 12, 2000, now abandoned.

BACKGROUND OF THE INVENTION

1. Field of the Invention

The present invention relates in general to tree stewardship and in particular to methods and mixtures for treating distressed trees.

2. Description of the Related Art

Across the Southern United States, the old growth forest is typically hardwoods such as Oaks, Elms, Hickory, Pecan, Bois d'ark, Hackberry, Ash, and the like. Unfortunately, where "progress", in the form of roads, homes, schools, and commercial construction meets the old growth forest, these trees are often subject to an adverse physiological reaction as a result of root system damage. This is particularly true with respects to the Post Oak (*Quercus Stellate*) which often dies in response to root system encroachment.

Most trees in the Southern forest react to the encroachment of construction in reasonably direct proportion to the percentage of the root system that is damaged. Usually the damage to the root system causes general injury a tree's health or slows its growth markedly. Not so with the Post Oak. Sometimes even small encroachments, such as a sidewalk across about ten-percent of its root area, result in the death of the tree. A few survive (far fewer than 50%), but most succumb in 1–7 years, a process which has been recently accelerated by harsh summers, such as those of 1998, 1999, and 2000. Indeed, the effects of sustained drought are as devastating a cause of shock as roots being cut or encroached upon.

The Post Oak is a magnificent wild organism. It grows only from acorns and almost never can be transplanted. It grows on dry ground, can weather drought, and its thick bark makes the tree resistant to wild fires, decay, and borers and other insects. Notwithstanding, Post Oaks are still highly sensitive to human encroachment, and thus require care and attention whenever such encroachment on the Post Oak's domain begins to cause distress.

Thus, methods and mixtures for treating distressed trees, and in particular distressed Post Oaks, are required.

SUMMARY OF THE INVENTION

According to the principles of the present invention, a method of treating a distressed tree is disclosed which includes the steps of creating a mixture comprising a fertilizer and a growth hormone and applying the mixture to a root area of the distressed tree.

Advantageously, these principles can be used to relieve the distress experienced by a wide variety of trees, including the most sensitive of these, namely, the Post Oak. The mixtures and methods disclosed herein are easy to apply; and can be provided to the consumer, in one embodiment, in kit form. The preferred fertilizers and root growth hormones are also readily available commercially.

BRIEF DESCRIPTION OF THE DRAWINGS

For a more complete understanding of the present invention, and the advantages thereof, reference is now made to the following descriptions taken in conjunction with the accompanying drawings, in which:

FIG. 2 is a flow chart illustrating an exemplary method of treating a distressed tree in accordance with the principles of the present invention.

DESCRIPTION OF THE PREFERRED EMBODIMENTS

Figure 1:
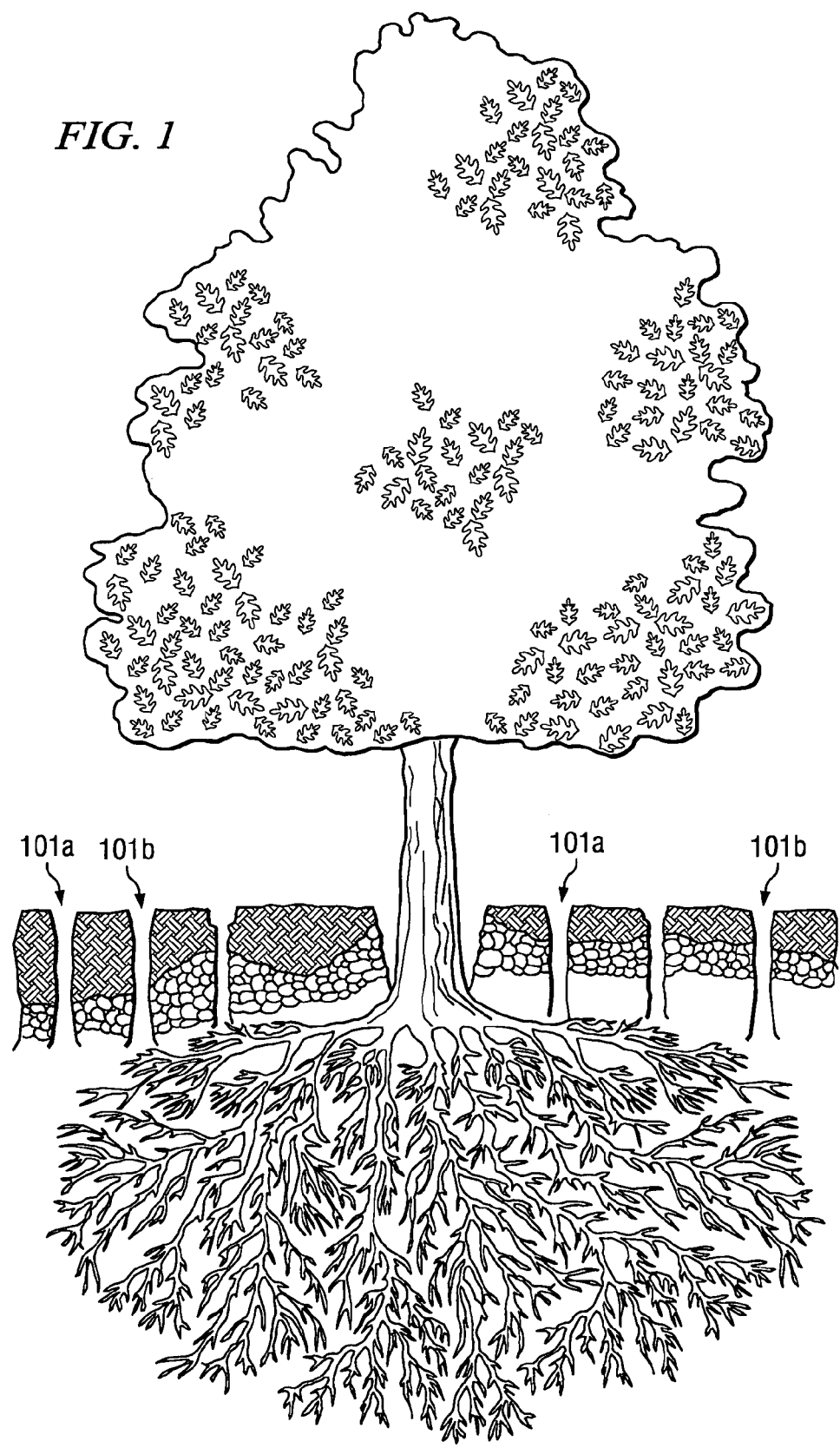
FIG. 1 is a diagram of an exemplary Post Oak, including the above ground portions (trunk, branches and leaves) and the below ground portions, namely the root system.

The principles of the present invention and their advantages are best understood by referring to the illustrated embodiment depicted in FIG. 1—of the drawings, in which like numbers designate like parts.

FIG. 1 is a diagram of an exemplary Post Oak, including the above ground portions (trunk, branches and leaves) and the below ground portions, namely the root system. A single idealized tree is shown for clarity, although the microenvironments in which these trees can be found are numerous. For example, Post Oaks can be found in cross timbers forest tangles, twisted and bent in order to gain their place in the sunlight. They are also found as wild hemispherical masses of foliage with the lower limbs intact and close to the ground, in open meadows and similar eco-structures. Moreover, Post Oaks can stand in groves hundreds of years old, with their lower limbs broken yet forming a full canopy over an often hardwood littered floor.

Post Oaks evoke all the qualities associated with oaks: strength, durability, character and toughness. They often survive even when other species of trees have been burned away by wild fires or killed by disease. Yet despite its strong reputation, the Post Oak is particularly susceptible to human "progress".

A drive past almost any new construction site across the Southern United States where old growth hardwoods still exist, often reveals giant leafless, dried-out, brittle, dead Post Oaks. Most tree experts agree that these deaths are not caused by parasites or a tree illness, but by insufficient water reaching the tips of the limbs. In these cases, the two most likely functions interrupted are water intake by the root system or delivery of water to the leaves.

It is fairly easy to rule out a problem in the water transport system if the trunk is intact or not otherwise damaged in any observable way. Moreover, the roots often appear healthy on examination. However, most of the tree's absorption of water and minerals from soil takes place in root hairs, because they make up more than 95 percent of the total surface area of the roots that can absorb. Additionally, distinction must be made between roots that can and cannot absorb water. Roots larger than about a fourth the diameter of one's little finger are not capable of absorbing water. Roots that have grown to that size or larger have formed a cork layer over the surface, which precludes any absorption. In fact, very little absorption occurs in roots after much more than an inch from the growing tip.

When a Post Oak's root area is cut or disturbed, as a reaction, it begins to produce fewer and fewer new cells at the root tip. In other words, the tree's production of new roots slows down. This reduces the number of root hairs, which reduces the absorptive capacity of the tree. As the slow-down continues, the tree's root system can support fewer and fewer leaves, and the continuing decline in leaves provides less food for making new roots. In turn, thinning of the canopy at the top results; the stress of the dwindling food supply causes the profusion of new leafy twigs or water sprouts on large limbs, instead of where they should grow, along the newer, smaller branches. This gives the tree the appearance of having green "fur" on its large limbs. This leafy "fur" on large branches of Post Oaks is a clear signal that the Post Oak is under serious stress. Soon, all leaf production ceases, and the tree dies.

The principles of the present invention provide chemical mixtures and methods for preventing and reversing damage to Post Oaks caused by human incursion and similar stresses. This treatment is effective on other tree species as well, with the proper modification for watering requirements. Advantageously, these principles provide the owners and stewards of these trees an alternative to the painful and costly process of watching the trees die, taking them down, and replanting. It means that in many cases the tree and shade are preserved to walk into or linger beneath on those especially hot days, even in view of human encroachment.

A preferred method 200 of treating a distressed tree is illustrated diagrammatically in FIG. 2. At Step 201, one or more holes are opened in the root area of the tree being treated. Preferably, these holes are opened or drilled at points around the periphery of the tree canopy approximately spaced by 18 inches. At each point three holes are opened, one approximately at the canopy line, another approximately 18 inches inside the canopy line and another approximately 18 inches outside the canopy line. In other words, the holes form a series of concentric rings around the periphery of the tree.

A pair of such holes 101a,b is shown in FIG. 1 for reference. This can be done in any one of a number of different ways. For example, the hole can be opened using manual implements, such as shovels or trowels. In one preferred method, the necessary holes are opened using a jet of water applied under pressure through a nozzle or probe. This method is particularly useful when the treatment mixture discussed below is in liquid form.

At Step 202, the treatment mixture is prepared. This mixture can be in powdered or liquid form and comprises a root growth hormone, a fertilizer, and optionally a fungicide. Exemplary root growth hormones include naphthalene acetic acid, 3-idolebutyric acid, and derivatives thereof. For example, one commonly available root growth hormone is a 0.1% naphthalene acetic acid (NAA) available from Schultz. Another commonly available mixture is a 0.1% indolebutyric acid (IBA) mixture sold under the tradename ROOTONE by Garden-tech.

An exemplary fertilizer has a nitrogen content in the range from about 10 to about 25 percent by weight, a phosphorous content in the range from about 5 to about 20 percent by weight, and a potassium content in the range from about 5 to about 20 percent by weight.

An exemplary optional fungicide is tetramethylthiuramdisulfide (Thiram) in a 4% by weight powder mix.

In the preferred powered embodiment, the mixture hormone—fertilizer mixture is composed of 2 ounces mixed with 20 pounds of commercially available fertilizer.

At Step 203, the mixture is applied to the holes opened in the root area of the tree under treatment. For dry formulations, approximately 2 ounces (56.4 grams) of the hormone—fertilizer mixture can be directly introduced into holes 101 by hand or machine. For 56.4 grams of mixture described above, the hormone dosage is approximately 0.355 milligrams per hole.

Liquid formulations of the growth hormone are also commercially available, typically with a concentration of 0.004% or 0.004 grams per liter of solution. In this case, to obtain a dosage of approximately 0.355 mg per hole, approximately 88.75 milliliters of hormone solution are required per hole. This equates approximately 3 ounces of 0.004% liquid per hole. A number of liquid fertilizers having the general characteristics described above are commercially available.

For liquid formulation or for a powdered formulation dissolved or suspended in a liquid, a water jet can be inserted into the soil, without the need to create a hole at Step 201. In this case, the hormone—fertilizer mixture is directly pumped into the ground using water flow such that the root area is saturated with the solution.

At Step 204, a watering program is carried out following chemical treatment of the tree. This program is designed to meet the need of the particular tree being treated, and accounts for such factors as weather and soil conditions. Specifically, watering occurs in a cycle of saturation and drying out. The reason for this is that all is tree roots, including Post Oak roots, need oxygen. A constant saturation of the soil deprives the root of oxygen and the root dies, moreover if insufficiently dried out; the root becomes susceptible to attack by bacteria and fungi.

On the other hand, the water applied to the tree root area must be sufficient to saturate the soil in the area that the plant's roots exist to a depth of 8 to 10 inches.

The watering plan can use apparatus and systems such as automated irrigation systems, tanks or reservoirs, optionally with advertising attached, hoses and soaker hoses, water wagons, and tanker trucks.

Incidental to the application of the combination of a root growth hormone-fertilizer-fungicide mixture but part of the overall tree treatment is the provision for the roots to have the capability to do gas exchange. This "aeration" is provided by the hole to root level left by the method of application or by a hole to root level made in addition to the method of application. For instance, the hormone-fertilizer-fungicide mixture can be put as a powder into a drilled hole, or driven as a pellet into the ground to the depth of the root system making a hole as applied, or pumped as a liquid solution into the ground making a hole as applied.

In sum, according to the inventive concepts, the roots of distressed trees are treated with specific chemicals and combinations of those chemicals that stimulate the growth of the roots and thus increasing the capacity of the plant to absorb water.

The application of the root growth hormone-fertilizer-fungicide mixture can be done as a commercial service. Moreover, the hormone-fertilizer-fungicide mixture implements for opening the holes in the root area, and instructions for properly implementing the method can be supplied as a kit. These kits are particularly advantageous to those wishing to perform the application themselves, including individual property owners, tree stewards, as well as independent contractors who will treat trees as part of their construction or landscaping, business.

These kits are designed specifically for rescuing distressed and declining trees. Advantageously, the kits facilitate the delivery of the appropriate compounds and tools to insure the effectiveness of the tree treatment and care. In the preferred embodiment, an exemplary kit contains a useful amount of the a root growth hormone/fertilizer combination in a deliverable form such as powder, pellets, or liquid, and a manual, directions, or instructions for use of the kit in the treatment and care of distressed and declining trees. This can be either written, video, or a mass storage method an example of which is a compact disk. Additionally, tools for measurement and delivery of the combination of a root growth hormone and fertilizer to the root system of the tree to be treated are also provided as part of the kit. Examples of these include water drills, a system for driving pellets, or a system for delivery of a liquid solution. The items comprising the kit are grouped together such a box, bag, or shrink wrapping. Marketing, ordering, and reorder information either separately or in the manual or on the box, bag, or wrapping.

In sum, the purpose of this "tree growth" or "tree treatment" or "tree rescue" kit would be to provide an affordable, effective unit of the combination of a root growth hormone and fertilizer for homeowners and business people.

Although the invention has been described with reference to specific embodiments, these descriptions are not meant to be construed in a limiting sense. Various modifications of the disclosed embodiments, as well as alternative embodiments of the invention will become apparent to persons skilled in the art upon reference to the description of the invention. It should be appreciated by those skilled in the art that the conception and the specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

It is therefore, contemplated that the claims will cover any such modifications or embodiments that fall within the true scope of the invention.

What is claimed:

1. A method of treating a tree exhibiting a decline in health the tree having an established root system in the earth, said method comprising the steps of:
   creating, in a container, a mixture comprising a fertilizer and a growth hormone; and
   applying the previously created mixture from the container directly underground to the soil in the root system of the tree to treat the root system of the tree,
   wherein the growth hormone is selected from the group consisting of naphthalene acetic acid and 3-indolebutyric acid,
   wherein the step of applying the mixture comprises the step of applying the mixture directly underground through holes drilled at points around the periphery of the tree canopy,
   wherein the step of applying the mixture comprises the step of applying the mixture directly underground through holes drilled at points around the periphery of the tree canopy spaced apart by substantially 18 inches.

2. The method of claim 1, further comprising the steps of:
   watering the tree to saturate the soil to a depth of 8 to 10 inches,
   allowing the soil in the root system of the tree to dry out over time so as to prevent bacteria and fungi from attacking the root, and
   re-watering the tree to saturate the soil to a depth of 8 to 10 inches.

3. The method of claim 2, wherein the fertilizer has a nitrogen content in the range of about 10 to about 25 percent by weight, a phosphorous content in the range of about 5 to about 20 percent by weight, and a potassium content in the range of about 5 to about 20 percent by weight.

4. The method of claim 3, further comprising the step of:
   leaving intact the holes drilled at points around the periphery of the tree canopy so as to aerate the root system of the tree and aid in root growth.

5. The method of claim 4, wherein said step of creating a mixture further comprises the step of adding a fungicide.

6. The method of claim 5, wherein said fungicide comprises the tetramethylthiuramdisulfide.

7. A method for treating a distressed tree planted in the earth, the distressed tree exhibiting a decline in health, the tree having an established root system in the earth, said method comprising the steps of:
   creating a hole in the soil in a root area of a tree; and
   applying directly underground a previously prepared mixture comprising a fertilizer and a root growth hormone in the hole created in a subterranean root area of the tree,
   wherein the root growth hormone is selected from the group consisting of naphthalene acetic acid and 3-indolebutyric acid,
   and further comprising the steps of:
   watering the distressed tree to saturate the soil to a depth of 8 to 10 inches,
   allowing the soil in the root system of the distressed tree to dry out over time so as to prevent bacteria and fungi from attacking the root, and
   rewatering the distressed tree to saturate the soil to a depth of 8 to 10 inches.

* * * * *